(12) United States Patent
Dubois et al.

(10) Patent No.: US 11,839,676 B2
(45) Date of Patent: *Dec. 12, 2023

(54) SYSTEM, METHOD, AND KIT FOR SELECTING AND PREPARING CUSTOMIZED COSMETICS

(71) Applicant: MEDISCA PHARMACEUTIQUE, INC., Saint-Laurent (CA)

(72) Inventors: Fanny Dubois, Montreal (CA); Panagiota Danopoulos, Montreal (CA)

(73) Assignee: MEDISCA PHARMACEUTIQUE Inc., Saint Laurent (CA)

( * ) Notice: Subject to any disclaimer, the term of this patent is extended or adjusted under 35 U.S.C. 154(b) by 1772 days.

This patent is subject to a terminal disclaimer.

(21) Appl. No.: 15/794,496

(22) Filed: Oct. 26, 2017

(65) Prior Publication Data

US 2018/0042838 A1 Feb. 15, 2018

Related U.S. Application Data

(63) Continuation of application No. 15/369,102, filed on Dec. 5, 2016, now abandoned, which is a continuation
(Continued)

(51) Int. Cl.
*G06Q 30/00* (2023.01)
*A61K 8/35* (2006.01)
(Continued)

(52) U.S. Cl.
CPC ............... *A61K 8/355* (2013.01); *A61K 8/31* (2013.01); *A61K 8/42* (2013.01); *A61K 8/64* (2013.01);
(Continued)

(58) Field of Classification Search
CPC ............ G06Q 30/613; G06Q 30/0631; G06Q 30/0613
See application file for complete search history.

(56) References Cited

U.S. PATENT DOCUMENTS 5,163,010 A 11/1992 Klein et al.
6,338,349 B1 1/2002 Robinson et al.
(Continued)

FOREIGN PATENT DOCUMENTS

CN 102078280 6/2011
EP 1093842 4/2001
(Continued)

OTHER PUBLICATIONS

Gupta, S., & Booten, K., Exotic Oils, Butters & Waxes: An array of Natural Materials from Asia, Africa and the Amazon Provide some Exciting Options for Formulators of Skin Care Products, 2005, Household & Personal Products Industry (Year: 2005).*
(Continued)

*Primary Examiner* — Matthew L Hamilton
(74) *Attorney, Agent, or Firm* — Fish & Richardson P.C.

(57) ABSTRACT

A kit for preparing a customized cosmetic includes at least one of five cosmetic bases. Each of the five cosmetic bases correspond to at least one of a plurality of primary categories. The kit additionally includes at least one cosmetic active ingredient for admixing with the at least one cosmetic base. The at least one cosmetic active ingredient corresponds to at least one of the plurality of primary categories or at least one of the plurality of secondary categories.

15 Claims, 2 Drawing Sheets

Related U.S. Application Data of application No. 14/603,552, filed on Jan. 23, 2015, now Pat. No. 9,522,112.

(60) Provisional application No. 61/930,712, filed on Jan. 23, 2014.

(51) Int. Cl.

| | |
|---|---|
| *A61K 8/92* | (2006.01) |
| *A61K 8/67* | (2006.01) |
| *A61K 8/64* | (2006.01) |
| *A61K 8/66* | (2006.01) |
| *A61K 8/68* | (2006.01) |
| *A61Q 19/00* | (2006.01) |
| *G06Q 30/0601* | (2023.01) |
| *A61K 8/73* | (2006.01) |
| *A61K 8/9789* | (2017.01) |
| *G06Q 50/04* | (2012.01) |
| *A61K 8/31* | (2006.01) |
| *A61K 8/42* | (2006.01) |
| *G06Q 99/00* | (2006.01) |

(52) U.S. Cl.
CPC .............. *A61K 8/66* (2013.01); *A61K 8/675* (2013.01); *A61K 8/676* (2013.01); *A61K 8/68* (2013.01); *A61K 8/73* (2013.01); *A61K 8/735* (2013.01); *A61K 8/922* (2013.01); *A61K 8/9789* (2017.08); *A61Q 19/00* (2013.01); *A61Q 19/005* (2013.01); *A61Q 19/007* (2013.01); *A61Q 19/008* (2013.01); *G06Q 30/0613* (2013.01); *G06Q 30/0621* (2013.01); *G06Q 30/0631* (2013.01); *G06Q 50/04* (2013.01); *G06Q 99/00* (2013.01); *A61K 2800/87* (2013.01); *A61K 2800/882* (2013.01)

(56) References Cited

U.S. PATENT DOCUMENTS

| | | | |
|---|---|---|---|
| 6,603,550 B1 | 8/2003 | Flynn et al. | |
| 6,782,307 B2* | 8/2004 | Wilmott | A61K 8/731 |
| | | | 700/239 |
| 7,174,310 B2 | 2/2007 | Bartholomew et al. | |
| 7,326,406 B2 | 2/2008 | Crook | |
| 7,445,372 B1 | 11/2008 | Engel et al. | |
| 8,017,137 B2 | 9/2011 | Bartholomew | |
| 8,109,875 B2 | 2/2012 | Gizewski | |
| 8,186,872 B2 | 5/2012 | Bartholomew et al. | |
| 8,352,070 B2 | 1/2013 | Bartholomew et al. | |
| 8,425,477 B2 | 4/2013 | Mou et al. | |
| 9,522,112 B2 | 12/2016 | Dubois et al. | |
| 2003/0091518 A1 | 5/2003 | Pauly | |
| 2003/0216941 A1 | 11/2003 | Berry | |
| 2004/0004309 A1 | 1/2004 | Sears | |
| 2004/0052826 A1 | 3/2004 | Fernandez-Kleinlein et al. | |
| 2004/0087888 A1 | 5/2004 | Digianfilippo et al. | |
| 2004/0161435 A1* | 8/2004 | Gupta | A61K 8/9717 |
| | | | 424/59 |
| 2005/0002978 A1 | 1/2005 | Barbara et al. | |
| 2005/0021174 A1 | 1/2005 | Wilmott et al. | |
| 2005/0240085 A1 | 10/2005 | Knoell et al. | |
| 2006/0010004 A1 | 1/2006 | Deckner | |
| 2006/0018867 A1 | 1/2006 | Kawasaki | |
| 2006/0036454 A1 | 2/2006 | Henderson | |
| 2007/0054261 A1 | 3/2007 | Sherman et al. | |
| 2007/0255595 A1 | 11/2007 | Nickell | |
| 2008/0243523 A1 | 10/2008 | Beilis | |
| 2008/0317733 A1 | 12/2008 | Azimi | |
| 2009/0076639 A1 | 3/2009 | Pak | |
| 2009/0187472 A1* | 7/2009 | Meloul | G07F 13/06 |
| | | | 707/E17.014 |
| 2009/0210322 A1 | 8/2009 | Stark | |
| 2010/0142755 A1 | 6/2010 | Brandewie et al. | |
| 2011/0030714 A1 | 2/2011 | Tijima et al. | |
| 2011/0305737 A1 | 12/2011 | Alexiades-Armenakas | |
| 2013/0023058 A1 | 1/2013 | Toumazou et al. | |
| 2013/0084259 A1 | 4/2013 | Lee | |
| 2017/0156999 A1* | 6/2017 | Harris | A45D 34/00 |
| 2017/0281526 A1* | 10/2017 | Dersh | A61B 5/444 |
| 2017/0360693 A1 | 12/2017 | Yakubov et al. | |
| 2018/0050224 A1 | 2/2018 | Burker-Colvin et al. | |
| 2018/0260871 A1 | 9/2018 | Harvill et al. | |
| 2018/0285952 A1 | 10/2018 | Lu | |

FOREIGN PATENT DOCUMENTS

| | | |
|---|---|---|
| JP | 200225338 | 9/2002 |
| KR | 20060109797 | 10/2006 |
| KR | 2007006288 | 1/2007 |
| WO | 0191600 | 12/2001 |
| WO | 0215735 | 2/2002 |
| WO | 2008035877 | 3/2008 |
| WO | WO 2018/102829 | 6/2018 |
| WO | WO 2020/232528 | 11/2020 |

OTHER PUBLICATIONS

Examiner's Report dated Dec. 4, 2019 in connection with Australian Patent Application No. 2015208796, 4 pages.

Examiner's Report dated Nov. 12, 2020 in connection with Australian Patent Application No. 2015208796, 7 pages.

Office Action dated Apr. 16, 2021 in connection with Korean Patent Application No. 10-2016-7023039 with English translation, 21 pages.

Examiner's Report dated May 3, 2021 in connection with Canadian patent application No. 2,974,608, 4 pages.

Examiner's Report dated Jan. 12, 2022 in connection with Canadian patent application No. 2,974,608, 6 pages.

Athar, M. et al., 'Taxonomic perspective of plant species yielding vegetable oils used in cosmetics and skin care products', African Journal of Biotechnology, 2005, vol. 4, pp. 36-44.

Fleck, C. A., et al., Advanced Skin Care—A Novel Ingredient, Journal of the American College of Clinical Wound Specialists, 2012, vol. 4, pp. 92-94.

Matsui, Y. et al., 'Extract of Passion Fruit (*Passiflora edulis*) Seed Containing High Amounts of Piceatannol Inhibits Melanogenesis and Promotes Collagen Synthesis', J. Agric. Food Chem., 2010, vol. 58, pp. 11112-11118.

Nayak, B. S. et al., 'Experimental Evaluation of Ethanolic Extract of Carapa guianensis L. Leaf for Its Wound Healing Activity Using Three Wound Models', Evidence-Based Complementary and Alternative Medicine, 2011, vol. 2011, pp. 1-6.

Extended European Search Report dated Jul. 7, 2017 in connection with European Patent Application No. 15740066.4, 11 pages.

Supplemental European Search Report dated Jul. 17, 2017 in connection with European Patent Application No. 15740066.4, 1 page.

United States Office Action dated Jun. 2, 2017 in connection with U.S. Appl. No. 15/369,102, 13 pages.

Examiner's Report dated Sep. 3, 2020 in connection with Australian Patent Application No. 2015208796, 6 pages.

Coastal Scents, "Make Your Own", p. 1, Aug. 29, 2013.

DIY Cosmetics, "Make-Up", p. 1, Aug. 28, 2013.

International Preliminary Report on Patentability dated May 1, 2015 in connection with International PCT patent application No. PCT/IB2015/050523, 6 pages.

Kanga, "What's new in cosmetic R&D, high performance products call for innovative formulating techniques and riovel materials too_", Household & Personal Products Industry, Mar. 1, 2004, v41, Newsroom Summaries, p. 6.

OFRA 2011-2012 catalog (accessed at https://issuu.com/ofracosmetics/docs/ofracosmeticscatalogue on Jul. 19, 2016).

Reisch, Marc S. "Designer Cosmetics: Ingredients makers take lessons from biotechnology to mastermind the atest in personal care", Chemical & Engineering News, Mar. 25, 2002, vol. 80, No. 12, pp. 16-21.

(56) References Cited

OTHER PUBLICATIONS

Search Report dated May 1, 2015 in connection with International PCT patent application No. PCT/IB2015/050523, 4 pages.
The Body Shop invents individually for the high street. Cosmetics International, v19, n235, p. 1(1), Sunday, Aug. 1, 2004.
Vitamin B3 Powder (accessed at https://www.amazon.comNitaminB3PowderNiacinamideUsp/dp/B0051VE5DQ#customerReviews on Jul. 19, 2016).
Written Opinion dated May 1, 2015 in connection with International PCT patent application No. PCT/IB2015/050523, 5 pages.

* cited by examiner

SYSTEM, METHOD, AND KIT FOR SELECTING AND PREPARING CUSTOMIZED COSMETICS

CROSS-REFERENCE TO RELATED APPLICATIONS

This application is a continuation of U.S. patent application Ser. No. 15/369,102, filed on Dec. 5, 2016, which is a continuation of U.S. patent application Ser. No. 14/603,552, filed on Jan. 23, 2015, now U.S. Pat. No. 9,522,112. This application also claims the benefit of U.S. Provisional Patent Application Ser. No. 61/930,712, filed on Jan. 23, 2014. The contents of the aforementioned applications are incorporated by reference herein.

FIELD

The present disclosure relates to a system, method, and kit for preparing non-medicated cosmetics for skin conditions, and more particularly to a system, method, and kit for preparing non-medicated customized cosmetics.

BACKGROUND

Cosmetic products are traditionally known to improve an appearance of a consumer. Certain cosmetic products are composed of cosmetic active ingredients that are clinically tested and non-medicated to specifically improve the appearance of various skin conditions. To obtain the cosmetic products composed of cosmetic active ingredients for skin conditions, a consumer receives professional advice or a professional skin consultation prior to buying the cosmetic products. Despite this professional advice, existing products may not be customized to the specific skin condition of the consumer.

Appropriately customizing cosmetic products for each individualized skin condition of the consumer can become complex. Certain methods of providing customized cosmetic products directly to a consumer are known. These methods often include overwhelming a consumer with a large number of products, ingredients, regimens, and/or components to arbitrarily choose from, manually mix and match, and manually apply to the skin of the consumer in multiple stages. These methods can be time consuming, superfluous, and may not address every concern of the consumer. Each of the products, ingredients, regimens, or components can be acquired by the consumer based on an evaluation conducted by the consumer themselves. However, consumers may lack the requisite knowledge for properly evaluating their own skin condition and/or become confused by the complexity of choosing from a large number of products.

Therefore, with a growing demand for cosmetic products with active ingredients to improve skin conditions, there is a continuing need for a kit, system, and method for preparing cosmetics for specific skin conditions that is simple, customizable, expedient, and involves an educated evaluation of a skin condition of a consumer. It would be advantageous if kits, systems, and methods for preparing cosmetics could be improved.

SUMMARY

In concordance with the instant disclosure, a kit, system, and method for preparing cosmetics for specific skin conditions of a consumer that is simple, customizable, expedient, and involves an educated evaluation of the skin condition of the consumer, has surprisingly been discovered.

According to an embodiment of the instant disclosure, a kit for preparing a customized cosmetic is disclosed. The kit includes at least one of five cosmetic bases. Each of the five cosmetic bases correspond to at least one of a plurality of primary categories. The kit additionally includes at least one cosmetic active ingredient for admixing with the at least one cosmetic base. The at least one cosmetic active ingredient corresponds to at least one of the plurality of primary categories or at least one of a plurality of secondary categories.

According to another embodiment of the instant disclosure, a method for preparing a customized cosmetic is disclosed. The method included the steps of evaluating and categorizing a skin condition of a consumer by an evaluator through an evaluation system. The skin condition is categorized into at least one primary category and at least one secondary category. The evaluator then selects at least one cosmetic base corresponding to the at least one primary category of the categorized skin condition of the consumer. The evaluator also selects at least one cosmetic active ingredient corresponding to the at least one primary category or the at least one secondary category of the categorized skin condition of the consumer. The method additionally includes the step of recommending a formulation for the customized cosmetic by the evaluator. The formulation includes specific quantities of the at least one cosmetic active ingredient. The at least one cosmetic active ingredient is then admixed with the at least one cosmetic base according to the formulation to form the customized cosmetic with a mixing apparatus, before provision of the end product to the consumer.

According to yet another embodiment of the instant disclosure, a system for preparing customized cosmetics is disclosed. The system includes an evaluation system and a kit. The evaluation system includes a plurality of primary categories and a plurality of secondary categories. The evaluator evaluates and categorizes a skin condition of a consumer into at least one of the plurality of primary categories and at least one of the plurality of secondary categories. The evaluator recommends a formulation for preparing the customized cosmetic. The kit includes at least one of five cosmetic bases and at least one cosmetic active ingredient for preparing the customized cosmetic according to the formulation. Each of the five cosmetic bases corresponds to at least one of the plurality of primary categories. The at least one cosmetic active ingredient corresponds to at least one of the plurality of primary categories or at least one of the plurality of secondary categories.

BRIEF DESCRIPTION OF THE DRAWINGS

The above, as well as other advantages of the present disclosure, will become readily apparent to those skilled in the art from the following detailed description, particularly when considered in the light of the drawings described herein.

DETAILED DESCRIPTION

The following detailed description and appended drawings describe and illustrate various embodiments of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical unless otherwise disclosed.

Figure 1:
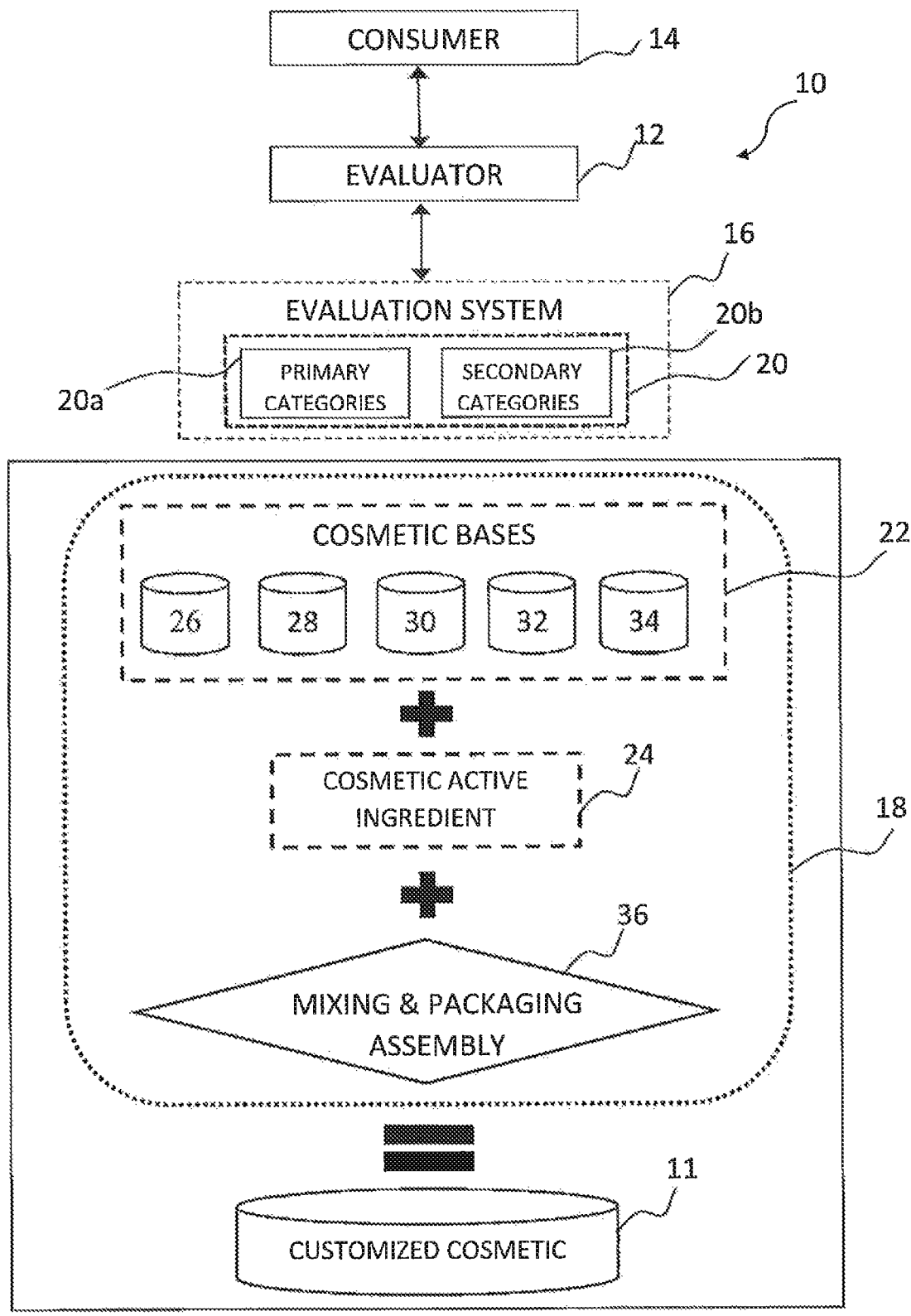
FIG. 1 is a schematic diagram of a system for preparing customized cosmetics, the system including a kit with particular cosmetic bases and cosmetic active ingredients.

In FIG. 1, a system 10 for preparing a customized cosmetic 11 is illustrated. As used herein, the term "customized cosmetic" describes a science-based cosmetic that provides beneficial topical actions to the skin. The customized cosmetic 11 of the present disclosure may be a non-medicated product that does not require a prescription. The customized cosmetic 11 is a product that is composed of carefully selected, clinically tested non-medicated cosmetic active ingredients that improve the appearance of various non-severe skin conditions.

The system 10 includes an evaluation system 16 for use by an evaluator 12 and a consumer 14, and a kit 18. The evaluator 12 receives information about the consumer 14 pertaining to skin conditions of the consumer 14 such as skin types and skin concerns of the consumer 14. The evaluator 12 provides an evaluation through the evaluation system 16 and categorizes the skin condition of the consumer 14 into categories 20. Based on the evaluation and categorization through the evaluation system 16, the evaluator 12 provides a recommended formulation for a customized cosmetic 11 to the consumer 14. The kit 18 is utilized to prepare the customized cosmetic 11 based upon the recommended formulation. The kit 18 can include cosmetic bases 22 and cosmetic active ingredients 24 for formulation of the customized cosmetic 11. The kit 18 can further include a mixing and packing assembly 36 to mix and package the customized cosmetic 11.

In certain embodiments, the evaluator 12 may be a healthcare professional, a licensed dermatologist, a medical physician, or a person trained in providing "behind-the-counter" products, as non-limiting examples. In other examples, the evaluator 12 can be a beautician, cosmetologist, esthetician, skin care provider, or any other person concerned with improving the appearance of various skin conditions of the consumer 14. The evaluator 12 is trained in at least selecting appropriate non-medicated customized cosmetics 11 based on the skin condition of the consumer 14.

The consumer 14 can be any person with a non-severe skin condition such as: oily skin; skin prone to imperfections or blemishes; dehydrated skin; sensitive skin; aging skin; skin requiring cosmetic maintenance; skin requiring recovery after surgery; or a combination thereof, for example. It is understood other non-severe skin conditions that may require customized cosmetics 11 can be contemplated, where non-severe skin conditions are skin conditions that do not require a dermatologist or medical physician. It is further understood that "condition" can include an aesthetic improvement.

The categories 20 of the skin condition of the consumer 14 can include primary categories 20a and secondary categories 20b. For example, the primary categories 20a can be based on the skin types and primary skin concerns of the consumer 14. The primary categories 20a can include the following skin types, for example: very dry skin, dry skin, normal skin, combination of oily and dry skin, oily skin, and very oily skin. The primary categories 20a can include the following primary skin concerns, for example: cosmetic procedure maintenance, aging, post procedure recovery, moisture, sensitivity, oily skin and/or blemishes. Additional or other varying skin types and/or primary skin concerns can be contemplated, as desired. Additionally, the primary categories 20a can be based upon other criteria besides skin types and primary skin concerns of the consumer 14 without departing from the scope of the present disclosure.

The secondary categories 20b, which can be subsidiary categories dependent on the primary categories 20a, can be based on secondary skin concerns of the consumer 14. For example, if the primary skin concern of the consumer 14 is aging, the secondary categories 20b can include the following secondary skin concerns relating to aging: wrinkle prevention, wrinkle plumping, photo-aging, dark spot, excess oil, moisture and sensitivity. In another example, if the primary skin concern of the consumer 14 is cosmetic procedure maintenance, then the secondary categories 20b can include types of cosmetic procedures. Additional or other varying secondary skin concerns can be contemplated, as desired, that are dependent on or independent from the primary categories 20a. It is understood additional categories or sub-categories in addition to the primary categories 20a and the secondary categories 20b can be contemplated, as desired.

The evaluation system 16 can assist the evaluator 12 in manually performing the evaluation and categorization of the skin condition of the consumer 14. The evaluation system 16 can be a list of key pre-determined questions asked to the consumer 14, references to a selection chart, use of devices such as optical skin analyzers and scanners, a downloadable computer program, an application for analyzing and evaluating skin conditions, or any combination thereof. In certain embodiments, the evaluation system 16 can be complemented by using an automatic skin imaging system. It is understood the evaluation system 16 can be any tool, device, or program, as desired to assist the evaluator 12 during the evaluation.

In a non-limiting example, the evaluation system 16 includes a questionnaire that can be subjectively completed by the consumer 14 and a corresponding selection guide utilized by the evaluator 12. The questionnaire includes questions or options pertaining to the skin type of the consumer 14, the primary skin concerns of the consumer 14, and the secondary skin concerns of the consumer 14. The consumer 14 identifies from the options that correspond to their individualized skin conditions. The consumer 14 selects and/or ranks their corresponding skin type and corresponding primary skin concerns. The consumer 14 can select from and/or rank multiple skin types and/or primary skin concerns corresponding to their individualized skin conditions. For example, the consumer 14 may identify their skin type as dry and rank their top two primary skin concerns, based on importance, as moisture being the most important primary skin concern and aging being the second most important primary skin concern.

After selecting from and/or ranking the skin types and the primary skin concerns, the consumer 14 can additionally identify and/or rank further secondary skin concerns pertaining to the primary skin concerns chosen and/or ranked. For example, if the consumer 14 ranked moisture as one of their most important primary skin concerns, the consumer 14 may then be instructed by the questionnaire to rank secondary skin concerns in order of importance and/or select an intensity of the secondary skin concerns relating to moisture. In another example, if the consumer 14 ranked aging as one of their most important primary skin concerns, the consumer 14 may then be instructed to select and/or rank the secondary skin concerns or select an intensity of the secondary skin concerns relating to aging. It is understood that alternate or additional personal or identifying information besides the skin types, the primary skin concerns, and the secondary skin concerns, can be included in the questionnaire, as needed by the evaluator 12, to determine the customized skin condition of the consumer 14.

According to the non-limiting example, the corresponding selection guide is utilized by the evaluator 12 to select a cosmetic base 22 and at least one cosmetic active ingredient 24 for providing the generated or recommended formulation of the customized cosmetic 11 to the consumer 14. The selection guide corresponds to the selections generated on the questionnaire and includes the categories 20 for categorizing the skin condition of the consumer 14. The selection guide includes a cosmetic base chart. The base chart includes the primary categories 20a based upon the skin types and the primary skin concerns. Each of the cosmetic bases 22 corresponds with or aligns with at least one of the primary categories 20a. The evaluator 12 then utilizes the cosmetic base chart of the selection guide to select one of the cosmetic bases 22.

The selection guide can also include a cosmetic active ingredient chart for choosing at least one of the cosmetic active ingredients 24 to be admixed to the selected cosmetic base 22. The cosmetic active ingredient chart includes the secondary categories 20b based upon the secondary skin concerns. Each of the cosmetic active ingredients 24 and their specified quantities corresponds with or aligns with at least one of the secondary categories 20b. The evaluator 12 then utilizes the cosmetic active ingredients chart of the selection guide to select one or more of the cosmetic active ingredients 24 and amounts thereof to be admixed to the selected cosmetic base 22. It is understood any number or quantity of the cosmetic bases 22 and/or cosmetic active ingredients 24 can be chosen depending on the skin types, the primary skin concerns, and the secondary skin concerns of the consumer 14, as desired. For example, the evaluator 12 can select a single cosmetic base 22 based on the most important primary skin concern of the consumer, and a plurality of cosmetic active ingredients 24 based on both the primary and secondary skin concerns of the consumer 14. In another example, the evaluator 12 can select two cosmetic bases 22 based on the two most important primary skin concerns of the consumer 14, and a single cosmetic active ingredient 24 based on the secondary skin concerns of the consumer 14. Other combinations of the cosmetic bases 24 and the cosmetic active ingredients 24 may also be selected according to the present method, as desired.

Once the cosmetic base 22 and the cosmetic active ingredients 24 are selected by the evaluator 12, the recommended formulation for the customized cosmetic 11 can then be provided to the consumer 14. The recommended formulation includes a list of the quantities of the cosmetic bases 22 and the cosmetic active ingredients 24 recommended for the customized cosmetic 11. The amounts of each of the cosmetic bases 22 and the cosmetic active ingredients 24 can be given in milliliters or grams, for example. Although other units of measurement can be contemplated, as desired.

The recommended formulation for the customized cosmetic 11 can be manually compiled by the evaluator 12 with the aid of the evaluation system 16. However, the recommended formulation can be automatically populated by a computer system, for example, involving a processor that executes computer-executable instructions stored in a memory of the computer system for generating a formulation, based on information provided to the evaluator 12, such as the questionnaire prepared by the consumer 14. A training program for the evaluator 12 can be administered. The training program can train the evaluator 12 in skin biology and in cosmetic formulation and ingredients. Reference charts containing important information about each of the cosmetic bases 22 and the cosmetic active ingredients 24 can be provided to the evaluator 12 for reference.

The customized cosmetic 11 is then prepared and provided to the consumer 14 based on the recommended formulation provided by the evaluator 12. The customized cosmetic 11 includes one of the cosmetic bases 22 and at least one of the cosmetic active ingredients 24. The cosmetic base 22 can be one of a limited variety of bases such that each of the cosmetic bases 22 corresponds to at least one of the primary categories 20a of the skin condition of the consumer 14.

For example, as shown in FIG. 1, the cosmetic bases 22 are one of five bases including a light anti-aging cream base 26, a rich anti-aging cream base 28, a sensitive skin cream base 30, a moisturizing cream base 32, and an oily skin cream base 34. Each of the cosmetic bases 22 includes at least one essential cosmetic active ingredient 24 selected for at least one of the primary categories 20a of the skin condition of the consumer 14. Each of the cosmetic bases 22 may correspond to one or more of the primary categories 20a of the skin condition of the consumer 14. For example, the rich anti-aging cream base 28 may correspond to the primary categories 20a of very dry skin type with a primary skin concern of aging, very dry skin type with a primary skin concern of cosmetic procedure maintenance, dry skin type with a primary skin concern of aging, or dry skin type with a primary skin concern of cosmetic procedure maintenance. In another example, the oily skin cream base 34 may correspond to the primary categories 20a of very oily skin type with a primary skin concern of cosmetic procedure maintenance, very oily skin type with a primary skin concern of aging, or very oily skin type with a primary skin concern of moisture.

The light anti-aging cream base 26 and the rich anti-aging cream base 28 include ingredients that, alone or in combination, are configured to facilitate improvement of skin texture, hydration, and radiance, and militate against appearance of wrinkling when applied to the skin. The rich anti-aging cream base 28 may include ingredients in greater concentrations, or more intensive ingredients, for example, in comparison to the light anti-aging cream base 26. The sensitive skin cream base 30 includes ingredients that, alone or in combination, are configured to facilitate treatment of delicate skin and militate against redness and skin itching and tingling when applied to the skin. The moisturizing cream base 32 includes ingredients that, alone or in combination, are configured to facilitate improvement of skin texture and hydration, and militate against appearances of fine lines when applied to the skin. The oily skin cream base 34 includes ingredients that, alone or in combination, are configured to facilitate minimization of pores and militate against blemishes and skin shininess when applied to the skin.

As non-limiting examples, the light anti-aging cream base 26 may include the ingredients water, aloe barbadensis leaf juice, glycerin, dicaprylyl carbonate, dimethicone, myristyl myristate, radish seed oil, and glyceryl stearate. The rich anti-aging base 28 cream may include water, aloe barbadensis leaf juice, glycerin, dicaprylyl carbonate, dimethicone, *Mangifera indica* (mango) seed butter, glyceryl stearate SE, myristyl myristate, radish seed oil, behenyl alcohol, glyceryl stearate, and hydroxyethyl acrylate/sodium acryloyldimethyl taurate copolymer. The sensitive skin cream base 30 may include water, *Carapa guaianensis* seed oil, dicaprylyl carbonate, cetearyl alcohol, glycerin, hydrogenated polyisobutene, propylheptyl caprylate, cetyl alcohol, and phenoxyethanol. The moisturizing cream base 32 may include water, cetearyl alcohol, aloe barbadensis leaf juice, *Theobroma grandiflorum* seed butter, PPG-3 benzyl ether ethylhexanoate, glycerin, PPG-2 myristyl ether propionate, squalane, beheneth-30 phosphate, caprylic/capric triglyceride, and phenoxyethanol. The oily skin cream base 34 may include the ingredients water, propanediol, dicaprylyl carbonate, aloe vera barbadensis leaf juice, *Passiflora edulis* seed oil, bentonite, dimethicone, hydroxyethyl acrylate/sodium acryloyldimethyl taurate copolymer, PEG-75 shea butter glycerides, polymethyl methacrylate, glyceryl stearate, and PEG-100 stearate. One of ordinary skill in the art may select other ingredients for each cosmetic base 22, as well as suitable concentrations of the ingredients, as desired. It is understood that each cosmetic base 22 can contain alternate or additional cosmetic active ingredients 24 or other ingredients to facilitate improvement of the skin condition of the consumer 14.

The cosmetic active ingredients 24 are ingredients corresponding to the primary categories 20a and/or the secondary categories 20b and configured to benefit the skin of the consumer 14 or address secondary skin concerns of the consumer 14. The cosmetic active ingredients 24 can be admixed with the cosmetic bases 22 to "boost" the cosmetic base 22 to address the primary skin concerns and/or the secondary skin concerns of the consumer 14 or achieve specific benefits. Multiple cosmetic active ingredients 24 may be admixed in varying amounts with each of the cosmetic bases 22 to address varying or multiple primary skin concerns and secondary skin concerns of the consumer 14 or achieve multiple benefits.

For example, the cosmetic active ingredients 24 can be an octapeptide, an ingredient known to improve appearance of expression lines and wrinkles. The octapeptide can be used to correspond to the primary category 20a involving aging with the secondary category 20b of wrinkling, the primary category 20a of moisturizing with the secondary category 20b of wrinkles, or the primary category 20a involving cosmetic procedure maintenance where the procedure was botulinum toxin. In other non-limiting examples, the cosmetic active ingredients 24 can be any cosmetic active ingredient such as an antioxidant enzyme complex, a tetrapeptide and oligopeptide blend, a hyaluronic acid liposomes ingredient, a vitamin C derivative, or a vectorized co-enzyme Q10, known for anti-aging, anti-dark spots, or anti-wrinkling effects. The cosmetic active ingredient 24 can be a vectorized ceramides ingredient or a carob extract ingredient, known for moisturizing effects. The cosmetic active ingredient 24 can be a vegetal omega fatty acids ingredient, a tetrapeptide ingredient, or a polysaccharide ingredient, known to provide benefits for sensitive, red, or itchy skin. The cosmetic active ingredient 24 can be a triterpene gel or vitamin B3 known to improve skin shininess and imperfections. One of ordinary skill in the art may select other suitable active ingredients as the cosmetic active ingredients 24, as desired.

At least one of the cosmetic active ingredients 24 are admixed with one of the cosmetic bases 22 to form a customized cosmetic 11. The customized cosmetic 11 provided to the consumer 14 includes one of the cosmetic bases 22 corresponding to the primary category 20a of the skin condition of the consumer 14 and one or more cosmetic active ingredients 24 corresponding to the primary category 20a and/or the secondary category 20b of the skin condition of the consumer 14. According to one exemplary embodiment of the disclosure, the skin condition of the consumer 14 may be categorized into the primary category 20a of dry skin type with a primary skin concern of moisture and into the secondary categories 20b of excess oil and blemishes, dehydration, and mild dynamic wrinkles. According to this embodiment, the customized cosmetic 11 includes the moisturizing cream base 32 which corresponds to the primary category 20a of a dry skin type with a primary skin concern of moisture. The customized cosmetic 11 can also include predetermined quantities of the three cosmetic active ingredients 24 such as a triterpene gel ingredient, a carob extract ingredient, and a vectorized co-enzyme Q10 ingredient, each respectively corresponding to the secondary categories 20b of excess oil and blemishes, dehydration, and mild dynamic wrinkles.

The cosmetic active ingredients 24 and the cosmetic bases 22 can be mixed and packaged through a mixing and packaging assembly 36. The mixing and packaging assembly 36 can include various mixing apparatuses such as pestle and mortars, agitators, blenders, mixing systems, stirrers, impelling devices, and any other pharmaceutical type mixers as desired. The customized cosmetic 11 can be packaged 12 through the mixing and packaging assembly 36. The mixing and packaging assembly 36 can include various packaging materials dependent on the viscosity of the customized cosmetic 11 such as a jar or bottle, for example. Although other packaging materials can be used, as desired. Based on the recommended formulation provided by the evaluator 12, the customized cosmetic 11 can be mixed and packaged on-site by the evaluator 12 or an assembler at a facility of the evaluator 12 such as a pharmacy, physician's office, or salon for example. However, in other examples, the customized cosmetic 11 can be mixed and packaged by an off-site manufacturer or assembler based upon the recommended formulation provided by the evaluator 12, if desired.

With continuing reference to FIG. 1, it should be appreciated that the cosmetic active ingredients 24 and the cosmetic bases 22 may be provided to the evaluator 12, assembler, or manufacturer in the form of the kit 18, or individually, as desired. The kit 18 can include one or more of the cosmetic bases 22 and one or more of the cosmetic active ingredients 24. In certain embodiments, the kit 18 includes the selected cosmetic base(s) 22 and the selected cosmetic active ingredient(s) 24, in the specified quantities, according to the recommended formulation provided by the evaluator 12. In other embodiments, the kit 18 can generally include one or more of each of the light anti-aging cream base 26, the rich anti-aging cream base 28, the sensitive skin cream base 30, the moisturizing cream base 32, and the oily skin cream base 34, as well as a plurality of cosmetic active ingredients 24. In a particular embodiment, the kit 18 consists of the light anti-aging cream base 26, the rich anti-aging cream base 28, the sensitive skin cream base 30, the moisturizing cream base 32, and the oily skin cream base 34, and a plurality of cosmetic active ingredients 24, together with the evaluator system 16 for use by the consumer 14 and the evaluator 12 in preparing the customized cosmetic 11. Each of the cosmetic bases 22 and the cosmetic active ingredients 24 included in the kit 18 can be provided in bulk quantities, for forming the customized cosmetics 11 on an as needed basis, or in specified quantities, for forming the customized cosmetics 11 based upon specific formulations. The kits 18 can be provided to the evaluator 12, or to the third party manufacturer or assembler either prior to or subsequent to the evaluation by the evaluator 12.

Figure 2:
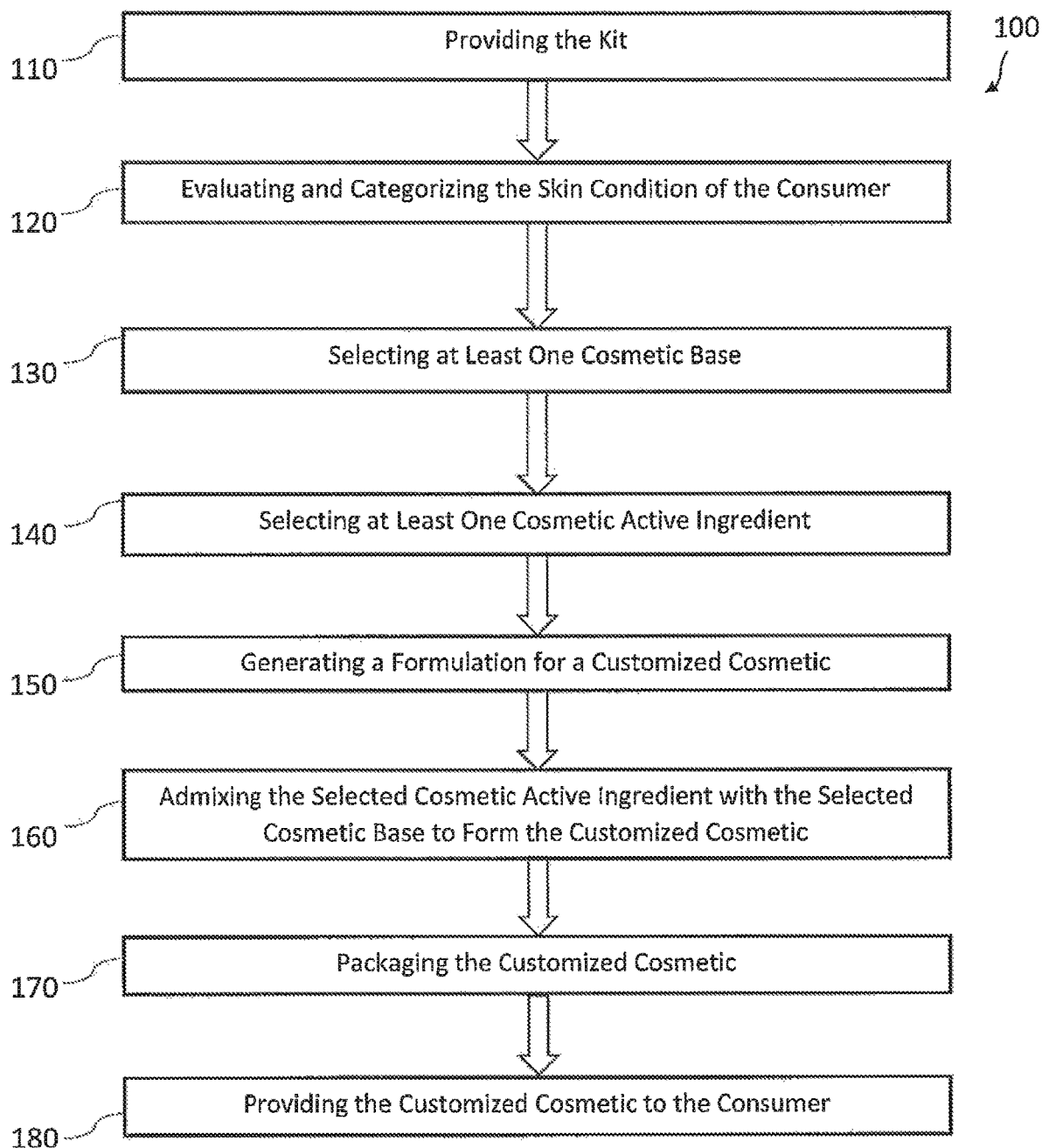
FIG. 2 is a flow diagram of a method of preparing customized cosmetics according to an embodiment of the invention.

FIG. 2 illustrates a method 100 of preparing customized cosmetics 11 according to an embodiment of the instant disclosure. In step 110, the kit 18 is provided to the evaluator 12, the manufacturer, or the assembler to form the customized cosmetic 11. As described hereinabove, the kit 18 includes one or more cosmetic bases 22 corresponding to one of the primary categories 20*a* and one or more cosmetic active ingredients 24 corresponding to one or more of the primary categories 20*a* and/or the secondary categories 20*b*. The kit 18 can include the cosmetic base 22 and the one or more cosmetic active ingredients 24 according to the recommended formulation provided by the evaluator 12 in step 140. The kit 18 can also include one or more cosmetic active ingredients 24 and one or more cosmetic active ingredients 24 in bulk quantities so that the specific quantities can be later administered into the specific quantities according to the recommended formulation provided by the evaluator 12 in step 140. It should be appreciated that the kit 18 can also include the evaluation system 16, such as client questionnaires and product selection guides to be used by the evaluator 12 when using the kit 18

In step 120, the skin condition of the consumer 14 is evaluated and categorized into categories 20 such as the primary categories 20*a* and the secondary categories 20*b*. As described hereinabove, the skin condition of the consumer 14 is evaluated and categorized into the categories 20 by the evaluator 12 through the evaluation system 16 based on information gathered from the consumer 14.

In step 130, the evaluator 12 selects one of the cosmetic bases 22 (e.g., the light anti-aging cream base 26, the rich anti-aging cream base 28, the sensitive skin cream base 30, the moisturizing cream base 32, and the oily skin cream base 34) corresponding to the primary category 20*a* of the categorized skin condition of the consumer 14. More than one cosmetic base 22 can be selected if the skin condition of the consumer 14 is categorized into more than one primary category 20*a*. The primary categories 20*a* can be based on the skin type of the consumer 14 and/or the primary skin concern of the consumer 14.

As non-limiting examples, if the skin condition of the consumer 14 was categorized under the primary category 20*a* of oily skin type with the primary skin concern of cosmetic procedure maintenance, the evaluator 12 selects the light anti-aging cream base 26 which corresponds to the primary category 20*a* of oily skin type with the primary skin concern of cosmetic procedure maintenance. In another non-limiting example, if the skin condition of the consumer 14 was categorized under the primary category 20*a* of very dry skin type with the primary skin concern of moisture, the evaluator 12 selects the moisturizing cream base 32 which corresponds to the primary category 20*a* of very dry with the primary skin concern of moisture. The evaluator 12 can select the corresponding cosmetic base 22 based on the information provided in the evaluation system 16.

In step 140, the evaluator 12 selects one or more cosmetic active ingredients 24 corresponding to the primary categories 20*a* and/or the secondary categories 20*b* of the skin condition of the consumer 14 to boost the selected cosmetic base 22. In a non-limiting example, if the skin condition of the consumer 14 is categorized in the primary category 20*a* of dry skin type with a primary skin concern of aging and the secondary category 20*b* of moderate to significant dark spots, the evaluator 12 may choose a vitamin C derivative ingredient as the cosmetic active ingredient 24, known for anti-aging and anti-dark spots effects. The vitamin C derivative ingredient is then added to the selected cosmetic base 22. As stated hereinabove, more than one cosmetic active ingredients 24 can be used if the skin condition is categorized into multiple primary categories 20*a* and/or multiple secondary categories 20*b* in order to boost the cosmetic base 22. The evaluator 12 can select the one or r corresponding cosmetic active ingredients 24 based on the information provided in the evaluation system 16.

In step 150, the evaluation system 16 generates a formulation for the customized cosmetic 11. The recommended formulation includes one of the cosmetic bases 22 corresponding to the primary category 20*a* of the categorized skin condition of the consumer 14 and one or more cosmetic active ingredient 24 corresponding to the primary category 20*a* and/or the secondary categories 20*b* of categorized skin condition of the consumer 14. Specific quantities or concentrations of each of the cosmetic bases 22 and the one or more cosmetic active ingredient 24 are included in the generated formulation.

In step 160, the one or more cosmetic active ingredients 24 selected in step 130 are admixed with the cosmetic base 22 selected in step 120 through the mixing and packaging assembly 36 to form the customized cosmetic 11 according to the generated formulation provided to the evaluator 12 in step 150. As stated hereinabove, the one or more cosmetic active ingredients 24 can be admixed with the selected cosmetic base 22 by the evaluator 12, on-site at the facility of the evaluator 12 by a separate assembler, or by an off-site manufacturer.

In step 170, the customized cosmetic 11 is packaged in package materials through the mixing and packaging assembly 36. In step 180, the customized cosmetic 11 is provided to the consumer 14. Additionally, technical support can be available to instruct or answer questions regarding any of the aforementioned steps.

Advantageously, the system, kit, and method for preparing customized cosmetics 11 for specific skin conditions, according to the present disclosure, is simple, customizable, and expedient. It involves an educated evaluation and categorization of the skin condition of the consumer 14, and provides the consumer 14 or the evaluator 12 with the ability to readily customize the cosmetic to address the unique individualized skin condition of the consumer 14. Each of the customized cosmetics 11 can provide one or more benefits to the skin of the consumer 14 based on the unique skin types, the primary skin concerns, and/or secondary skin concerns of the consumer 14.

While certain representative embodiments and details have been shown for purposes of illustrating the invention, it will be apparent to those skilled in the art that various changes may be made without departing from the scope of the disclosure, which is further described in the following appended claims.

What is claimed is:

1. A processor-implemented method for a skin care evaluation system, comprising:
   presenting to a user, via an input/output interface, an option to select a skin type, an option to select at least one primary skin concern and an option to select at least one secondary skin concern;
   receiving from the user, via said input/output interface, a selection of skin type, a selection of at least one primary skin concern and a selection of at least one secondary skin concern;
   selecting, by a processor, at least one cosmetic base from a plurality of cosmetic bases based on at least one of the selected skin type and the selected at least one primary skin concern, wherein the plurality of cosmetic bases comprise:
   a light anti-aging cream base having a first ingredient configured to militate against appearance of wrinkling when applied to skin of a consumer, wherein the first ingredient includes radish seed oil, a rich anti-aging cream base having a second ingredient configured to militate against appearance of wrinkling when applied to the skin, wherein the second ingredient includes *Mangifera indica* (mango) seed butter, a sensitive skin cream base having a third ingredient configured to militate against redness when applied to the skin, wherein the third ingredient includes *Carapa guaianensis* seed oil, a moisturizing cream base having a fourth ingredient configured to militate against appearances of fine lines when applied to the skin, wherein the fourth ingredient includes *Theobroma grandiflorum* seed butter, and an oily skin cream base having a fifth ingredient configured to militate against skin shininess when applied to the skin, wherein the fifth ingredient includes *Passiflora edulis* seed oil selecting, by the processor, at least one cosmetic active ingredient based on at least the selected at least one secondary skin concern; and generating, by the processor, a customized cosmetic formulation for the user that includes the at least one cosmetic base and the at least one cosmetic active ingredient.

2. The processor-implemented method defined in claim 1, wherein presentation of the option to select the at least one secondary skin concern is dependent on which skin type is selected via the option to select a skin type.

3. The processor-implemented method defined in claim 1, wherein presentation of the option to select the at least one secondary skin concern is dependent on which at least one primary skin concern is selected via the option to selected at least one primary skin concern.

4. The processor-implemented method defined in claim 1, wherein presentation of the option to select the at least one secondary skin concern is dependent on which skin type is selected via the option to select a skin type and on which at least one primary skin concern is selected via the option to select at least one primary skin concern.

5. The processor-implemented method defined in claim 1, further comprising: causing transmission of the customized cosmetic formulation to a manufacturer.

6. The processor-implemented method defined in claim 1, further comprising: causing production of a cosmetic product in accordance with the customized cosmetic formulation.

7. The processor-implemented method defined in claim 1, wherein selecting the at least one cosmetic base based on at least one of the selected skin type and selected at least one primary skin concern comprises identifying a primary category associated with the selected skin type and the selected at least one primary skin concern and selecting the at least one cosmetic base based on the at least one identified primary category.

8. The processor-implemented method defined in claim 1, wherein selecting the at least one cosmetic active ingredient based on at least the selected at least one secondary skin concern comprises selecting the at least one cosmetic active ingredient based on the selected skin type, the selected at least one primary skin concern the selected at least one secondary skin concern.

9. The processor-implemented method defined in claim 1, wherein selecting the at least one cosmetic active ingredient based on at least the selected at least one secondary skin concern comprises identifying a primary category associated with the selected skin type and the selected at least one primary skin concern, and selecting the at least one cosmetic active ingredient based on the identified primary category and the selected at least one secondary skin concern.

10. The processor-implemented method defined in claim 1, wherein the at least one primary skin concern comprises plural primary skin concerns and wherein selecting the at least one cosmetic base based on at least one of the selected skin type and the selected at least one primary skin concern comprises selecting plural cosmetic bases.

11. The processor-implemented method defined in claim 1, wherein the at least one secondary skin concern comprises plural secondary skin concerns and wherein selecting the at least one active ingredient based on at least the selected at least one secondary skin concern comprises selecting plural active cosmetic ingredient.

12. The processor-implemented method defined in claim 1, further comprising determining a respective quantity of the at least one cosmetic base based on at least one of the selected skin type and the selected at least one primary skin concern.

13. The processor-implemented method defined in claim 12, further comprising determining a respective quantity of the at least one cosmetic active ingredient based on at least one of the selected secondary skin concern.

14. The processor-implemented method defined in claim 13, wherein the generated customized cosmetic formulation includes the at least one cosmetic base and the at least one cosmetic active ingredient in their respective quantities.

15. A computer system comprising:
a memory storing computer-readable instructions;
a processor configured to execute the computer-readable instructions;
an input/output interface;
wherein execution of the computer-readable instructions by the processor results in the computer system:
presenting to a user via the input/output interface an option to select a skin type, an option to select at least one primary skin concern and an option to select at least one secondary skin concern;
receiving from the user via the input/output interface a selection of skin type, a selection of at least one primary skin concern and a selection of at least one secondary skin concern;
selecting at least one cosmetic base from a plurality of cosmetic bases based on at least one of the selected skin type and the selected at least one primary skin concern;
selecting at least one cosmetic active ingredient based on at least the selected at least one secondary skin concern;
generating a customized cosmetic formulation for the user that includes the at least one cosmetic base and the at least one cosmetic active ingredient; and
storing the customized cosmetic formulation in the memory, wherein the plurality of cosmetic bases comprise:
a light anti-aging cream base having a first ingredient configured to militate against appearance of wrinkling when applied to skin of a consumer, wherein the first ingredient includes radish seed oil,
a rich anti-aging cream base having a second ingredient configured to militate against appearance of wrinkling when applied to the skin, wherein the second ingredient includes *Mangifera indica* (mango) seed butter,
a sensitive skin cream base having a third ingredient configured to militate against redness when applied to the skin, wherein the third ingredient includes *Carapa guaianensis* seed oil, a moisturizing cream base having a fourth ingredient configured to militate against appearances of fine lines when applied to the skin, wherein the fourth ingredient includes *Theobroma grandiflorum* seed butter, and an oily skin cream base having a fifth ingredient configured to militate against skin shininess when applied to the skin, wherein the fifth ingredient includes *Passiflora edulis* seed oil.

\* \* \* \* \*